United States Patent [19]

Cassidy et al.

[11] 3,994,739
[45] Nov. 30, 1976

[54] REFRACTORY COMPOSITION WITH A BINDER AND A BLOATING INHIBITOR

[75] Inventors: John Edward Cassidy; Brian Schofield, both of Runcorn, England

[73] Assignee: Imperial Chemical Industries Limited, London, England

[22] Filed: Nov. 25, 1974

[21] Appl. No.: 526,924

[30] Foreign Application Priority Data
Dec. 3, 1973  United Kingdom............... 55972/73

[52] U.S. Cl.................................. 106/65; 106/55; 106/85; 106/90; 106/314
[51] Int. Cl.² .................. C04B 35/66; C04B 35/68; C04B 35/70
[58] Field of Search .................. 106/55, 65, 85, 90, 106/314

[56] References Cited
UNITED STATES PATENTS

| | | | |
|---|---|---|---|
| 3,663,251 | 5/1972 | Moren et al. | 106/314 X |
| 3,804,648 | 4/1974 | Birchall et al. | 106/56 |
| 3,870,737 | 3/1975 | Birchall et al. | 423/300 X |

OTHER PUBLICATIONS
Kirk-Othmer Encyclopedia of Chemical Technology, vol. 19 pp. 511, 541, 542.

*Primary Examiner*—Patrick P. Garvin
*Assistant Examiner*—John F. Niebling
*Attorney, Agent, or Firm*—Cushman, Darby & Cushman

[57] ABSTRACT

A mixture comprising at least one binder for a refractory aggregate which binder is a halogen-containing complex phosphate of aluminium containing one or more chemically-bound molecules of water and/or one or more chemically-bound oxygen-containing organic molecules, and at least one inhibitor which is an acetylenic alcohol having the structure

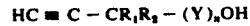

$$HC \equiv C - CR_1R_2 - (Y)_nOH \qquad 1.$$

where $R_1$ and $R_2$, which may be the same or different, are selected from hydrogen atoms and organic groups, Y is a divalent organic group, and $n$ is an integer in the range 2 to 30.

16 Claims, No Drawings

REFRACTORY COMPOSITION WITH A BINDER AND A BLOATING INHIBITOR

This invention relates to a mixture of a binder and an inhibitor for use in refractory compositions and to refractory compositions containing the mixture.

Refractory compositions comprising a mixture of a refractory aggregate, a binder which is an acidic material or which is a material capable of forming an acidic species, and a dispersant for the binder which is preferably a solvent for the binder, e.g. water, are known to suffer from certain disadvantages where the compositions contain metallic impurities. It is believed that in such compositions the acidic binder or acidic species formed from the binder reacts with the metallic impurities to liberate hydrogen. This leads to difficulties of storage of such compositions and, when the compositions are caused or allowed to set to produce shaped articles, bloating occurs in the articles which are produced. Bloating may be defined as the formation of voids in the shaped article. The formation of voids results in articles which may be somewhat misshapen, which have a decreased density, and which show a decrease in strength when compared with articles which have been produced from similar compositions but which are not bloated.

Thus, we have found that in refractory compositions in which the binder is a halogen-containing complex phosphate of aluminium bloating may occur if metallic impurities are present in the composition. Furthermore, we have now found that the extent of the bloating which occurs may be reduced and in some cases substantially eliminated if the composition includes an inhibitor having a particular structure.

The present invention provides a mixture comprising at least one binder for a refractory aggregate which binder is a halogen-containing complex phosphate of aluminium containing one or more chemically-bound molecules of water and/or one or more chemically bound oxygen-containing organic molecules, and at least one inhibitor which is an acetylenic alcohol having the structure $$HC \equiv C - CR_1R_2 - (Y)_n OH \qquad 1.$$

where $R_1$ and $R_2$, which may be the same or different, are selected from hydrogen atoms and organic groups, Y is a divalent organic group, and $n$ is an integer in the range 2 to 30.

In a further embodiment of the invention there is provided an essentially dry refractory composition comprising a refractory aggregate and a mixture of a binder and an inhibitor as herein described; and a settable refractory composition comprising a refractory aggregate, a mixture of a binder and an inhibitor as herein described, and a liquid diluent which is a solvent for the binder and the inhibitor and in which the binder and inhibitor form a solution. The liquid diluent is conveniently water or a diluent containing water, e.g. a mixture of water with an organic diluent.

The metallic impurities which may be present in the refractory compositions may arise in a number of different ways. For example, iron impurities may be present in the refractory aggregate and may arise from the use of steel balls in the ball mills used in the production of ball mill fines aggregate. Iron also is often present as an impurity in aggregate derived from crushed refractory bricks which have been recovered from furnaces. Metallic impurities other than iron may be present in refractory compositions. For example, chrome alumina slag may contain metallic chromium as a metallic impurity.

In the inhibitor having the structure (1) the groups $R_1$ and $R_2$ are suitably selected from hydrogen atoms and alkyl radicals having from 1 to 10 carbon atoms, e.g. methyl, ethyl and propyl. The groups $R_1$ and $R_2$ are conveniently both hydrogen atoms as the inhibitor may then be prepared from the readily available propargyl alcohol.

The group Y is preferably an oxyalkylene group as inhibitors containing such groups are especially effective in reducing the extent of bloating which occurs during use of the mixture of binder and inhibitor in refractory compositions containing metallic impurities. Thus, the inhibitor may, for example, have the structure:

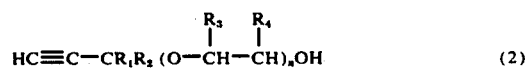

$$HC \equiv C - CR_1R_2 (O - CH - CH)_n OH \qquad (2)$$

with $R_3$ and $R_4$ on the CH groups, where $R_3$ and $R_4$, which may be the same or different, are selected from hydrogen atoms and organic groups.

Suitable organic groups include alkyl and branched alkyl groups having from 1 to 10 carbon atoms, e.g. methyl, ethyl, propyl and butyl; substituted alkyl groups, e.g. chloromethyl; and aromatic groups, e.g. phenyl. Preferably, both $R_3$ and $R_4$ are hydrogen or one of $R_3$ and $R_4$ is hydrogen and the other is an alkyl group, e.g. methyl. The oxyalkylene groups in the inhibitor of structure (2) may comprise a mixture of groups of different structures in some of which, for example, both $R_3$ and $R_4$ are hydrogen and in others of which, for example, one of $R_3$ and $R_4$ is hydrogen and the other is an alkyl group. The groups may be present in the form of random or block copolymers. Inhibitors in which the groups $R_3$ and $R_4$ are hydrogen or methyl or a mixture thereof, that is, in which the groups Y are oxyethylene or oxypropylene or a mixture thereof, are especially preferred as they may be prepared from the readily available ethylene oxide and propylene oxide or from a mixture thereof.

The inhibitor used in the present invention may comprise a mixture of compounds of structure (1) of differing values of $n$ such that in the mixture of inhibitors $n$ is on average not a whole number. Preferably, $n$ is on average in the range 2 to 12, e.g. approximately 7 as inhibitors having $n$ in this range are more readily prepared than inhibitors with higher values of $n$.

The acetylenic alcohols forming a part of the mixture of the present invention are substantially less volatile and substantially less toxic than is propargyl alcohol, and they are therefore much more conveniently usable as inhibitors than is propargyl alcohol. In view of its volatility propargyl alcohol would present substantial toxicity hazards, especially when subjected to elevated temperatures during use of refractory compositions. The hazards associated with the use of acetylenic alcohols present in the mixtures of the present invention are substantially less.

The acetylenic alcohol inhibitor of structure (1) may be prepared by reacting propargyl alcohol, or a substituted derivative thereof, with a source of the group Y. For example, where the group Y is an oxyalkylene group the inhibitor may be prepared by reacting propargyl alcohol, or a substituted derivative thereof, with an alkylene oxide, especially with an 1,2-alkylene oxide, e.g. a 1,2-alkylene oxide of the structure:

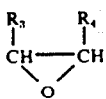

(3)

A mixture of two or more alkylene oxides may be used in the reaction.

The reaction may be carried out in the presence of a catalyst, e.g. a tertiary amine, an acid, an alkali metal hydroxide or alkaline earth metal hydroxide. Use of elevated temperatures and pressures may be required especially if inhibitors with high values of $n$ are desired.

In the mixture of binder and inhibitor the binder is a halogen-containing complex phosphate of aluminium containing one or more chemically-bound molecules of water and/or one or more chemically bound oxygen-containing organic molecules.

The complex aluminium phosphate binder may be made by reacting aluminium or an aluminium compound, for example, a halogen-containing aluminium compound, e.g. an aluminium halide, with phosphoric acid, a phosphoric acid ester or a compound capable of forming phosphoric acid or a phosphoric acid ester. Where aluminium or an aluminium compound other than a halogen-containing compound is used then it is also necessary to use in the reaction the corresponding halogen acid. The reaction is effected in the presence of water or an oxygen-containing organic molecule and the reaction mixture produced is generally a solution. The complex phosphate separated from the reaction mixture contains one or more chemically-bound molecules of water and/or oxygen-containing organic molecules. The preparation is preferably carried out at a temperature in the range 0° to 50° C and the complex phosphate may be separated by precipitation with a non-solvent, by concentration of the solution, or by freeze-drying or spray-drying of the solution. Chlorine is the preferred halogen although the complex may, for example be a bromine- or iodine-containing complex. The phosphate is preferably orthophosphate although meta- and pyrophosphate may be used.

Suitable oxygen-containing organic molecules include hydroxy compounds, esters, aldehydes and ketones, and particularly oxygen-containing organic molecules which form coordination compounds with aluminium salts. Preferred hydroxy compounds are aliphatic alcohols, for example aliphatic alcohols containing 1 to 10 carbon atoms; it is especially preferred to use aliphatic alcohols containing from 1 to 4 carbon atoms, for example ethyl alcohol.

The ratio of the number of gram atoms of aluminium to the number of gram atoms of phosphorus in the complex phosphate may vary over a wide range, for example from 1:2 to 2:1, more especially 1:1 to 2:1, but is preferably substantially 1:1, that is, in the range of about 0.8:1 to 1.2:1, as complex phosphates having this ratio decompose at low temperatures directly to form aluminium orthophosphate having greater chemical stability and refractoriness than aluminium phosphates formed from complex phosphates with other ratios. The ratio of the number of gram atoms of aluminium to the number of gram atoms of halogen in the complex phosphates may vary over a wide range, e.g. from 2:1 to 1:3 but is suitably substantially 1:1.

The complex aluminium phosphate may contain, for example, from 1 to 5 molecules of water and/or organic oxygen-containing molecule. Examples of suitable complex phosphates of aluminium are described in our British Pat. Nos. 1,322,722 and 1,322,724.

Examples of complex aluminium phosphates include the following.

a. That containing chlorine and ethyl alcohol and having the empirical formula $AlPClH_{25}C_8O_8$. The infra-red and X-ray characteristics of the compound are described in Example 1 of the aforesaid British Pat. No. 1,322,722. It may be referred to as ACPE.

b. That containing chlorine and water and having the empirical formula $AlPClH_{11}O_9$. The infra-red and X-ray characteristics of the compound are described in Example 1 of the aforesaid British Pat. No. 1,322,724. It may be referred to as ACPH.

c. That containing bromine and ethyl alcohol and having the empirical formula $AlPBrH_{25}C_8O_8$. The infra-red and X-ray characteristics of the compound are described in Example 3 of the aforesaid British Pat. No. 1,322,722. It may be referred to as ABPE.

It is to be understood, however, that these empirical formulae in no way imply any particular molecular structures for the complex phosphates.

Solid phosphate binders are often hygroscopic and we find that the binder when in admixture with the inhibitor may have a reduced tendency to hygroscopicity.

The mixture of complex aluminium phosphate binder and inhibitor may be produced merely by mixing of the solid binder and the inhibitor, e.g. by tumble-blending. A convenient method of producing the mixture is to add the inhibitor to a solution of the complex aluminium phosphate binder in a liquid diluent, for example to a solution as formed during preparation of the complex aluminium phosphate, and then separate the mixture from solution, for example, by precipitation with a non-solvent, by concentration of the solution, or by freeze-drying or spray-drying the solution. Preferably, the inhibitor is soluble in the liquid diluent. The concentration of binder in the solution may conveniently be in the range 1% to 50% by weight of the solution.

The amount of inhibitor which is present in the mixture will depend, inter alia, on the precise nature of the complex aluminium phosphate binder and on the amount of metallic impurities which are present in the refractory compositions. For a given binder and a given refractory aggregate the amount of inhibitor which is needed to produce a required amount of inhibition of bloating may be chosen by simple experiment by making up refractory compositions and varying the amount of inhibitor in the compositions so as to produce articles which contain the desired inhibition of bloating.

In the mixture of binder and inhibitor we find that in general at least 0.2% and generally from 0.2% to 5% of inhibitor by weight of the binder in the mixture is suitable, and preferably 0.5% to 4% by weight, although where the mixture is used in a refractory composition containing a relatively high proportion of metallic impurity proportions of inhibitor greater than 5% by weight of the binder, e.g. up to 10% by weight, may be required. Where the amount of metallic impurities is low then as little as 0.1% of inhibitor by weight of binder may be required.

The refractory aggregate is preferably an acidic or neutral aggregate although we do not exclude the use of a basic aggregate particularly an aggregate containing a proportion of a basic aggregate. A mixture of two or more different aggregates may be used. The refractory composition may also include a clay.

The refractory aggregate may be in any suitable form depending on the use to which the composition is to be put. Generally it is in the form of a powder but it may also be in the form of, for example, fibres, chips and flakes. Aggregates consisting of mixtures of coarse and fine particles are preferred since the strengths of products obtained using such mixtures are generally higher than the strengths of products obtained from compositions in which all the aggregate particles are of similar size.

The particle size of refractory aggregate may vary over a wide range depending on the intended use of the refractory composition. For example, where the settable refractory composition is to be used as a gunning mix it may be desired to use a relatively coarse powder whose particle size substantially falls within the range of 0.35 to 1.0 mm. Fine powders substantially the whole of which has a particle size of less than 0.05 mm may also be used.

For moulds used in investment casting, it is preferred to use a refractory powder at least 50% by weight of which has a particle size of less than 0.15 mm and more preferably less than 0.075 mm. On the other hand, the refractory aggregate may have a particule size of up to 2 cm or even greater.

Silica, alumina, for example, calcined alumina, tabular alumina and fused alumina, and zirconia are especially useful as refractory aggregates, as are zirconium silicates. Further examples of refratory aggregates which may be used include titanium oxide; aluminium silicates, e.g. sillimanite, andalusite, mullite and molochite; porcelain and china clays; carbides, e.g. silicon and tungsten carbides; nitrides, e.g. silicon and boron nitrides; boron; asbestos; ferric oxide; chromium oxide; chromite; mica; carbon, e.g. graphite.

The binder is suitably present in the essentially dry refractory composition in a proportion of 0.5% to 40% by weight of the composition. Proportions of 2% to 30% and 2% to 10% by weight of the composition are more preferred.

In the refractory compositions of the invention we find that in general at least 0.01% and generally from 0.01% to 1% of inhibitor by weight of aggregate is suitable, and preferably 0.02% to 0.5% by weight.

The amount of liquid diluent used in the settable refractory composition of the present invention should be such as to produce a composition having a consistency suitable for the particular application for which it is to used. Generally, the amount of liquid diluent will be in the range 0.5% to 25% by weight of the settable refractory composition, but it is preferably in the range 2% to 15% and more preferably in the range 5% to 10% weight of the composition.

The diluent is generally a solvent for the binder and for the inhibitor although the binder may be dispersed in the diluent, for example as a suspension, sol or gel. A preferred diluent is water. The diluent may be an organic liquid, for example, a polar organic liquid, e.g. methyl alcohol, ethyl alcohol, isopropyl alcohol, butyl alcohol, ethylene glycol or monoethyl ethyl ether. Mixtures of diluents may be used especially mixtures containing water. The essentially dry refractory composition may be made by mixing the refractory aggregate with the binder and with the inhibitor, or with the premixed binder and inhibitor, e.g. by tumble-blending or by grinding, and the settable refractory composition may be made by addition of the desired amount of diluent to the essentially dry refractory composition. Alternatively, the settable refractory composition may be made by mixing the refractory aggregate with a mixture of, and preferably with a solution of the binder in the diluent, optionally containing the inhibitor.

The settable refractory compositions may be used for a wide range of purposes including the production of shaped articles, especially by moulding, and also for purposes in which the hardening of the composition and its adhesion to its surroundings can be utilised, as for example as a coating composition, especially on metal substrates. The settable refractory compositions may also be used as a ramming mix, a pressing mix, a gunning mix, or as a mortar, cement of filler, for example for binding ceramics, but they are especially useful in high temperature applications, for example, in furnace walls and linings. The proportions of the components and the consistency of the settable refractory compositions may be chosen to make them of optimum value for the use intended. Shaped articles which may be produced from the settable refractory compositions include bricks, for example, furnace bricks, and other shaped structures, e.g. rectangular and hexagonal-shaped blocks; moulds, especially casting moulds; and sheets and other monoliths, for example, monolithic linings for high temperature applications.

The settable refractory composition may be converted to a hard, handleable product, that is it may be set, by heating the composition at an elevated temperature or by including in the composition a setting agent which reacts with the binder. If desired, setting of the composition may be achieved by a combination of heating and use of a setting agent. By suitable choice of setting agent the composition may be made cold-setting, that is, it may be made capable of being set in the cold to produce a cast product having sufficient green strength for the cast product to be handleable. A preferred setting agent is magnesium oxide as described in our copending application British Pat. No. 23885/72, now published as Netherlands pat. No. 7306526.

The product is then treated by heating, for example, at a temperature in the range 80° to 1200° C, to produce a refractory product. Suitably, this heating is carried out in two stages. In a first stage the product in its "green" state is dried, e.g. at a temperature in the range 80° to 250° C, and in a second stage the product is transferred to a furnace for high temperature firing, e.g. at a temperature of 800° to 1000° C to produce a refractory product.

When the settable refractory compositions are used as coating compositions they may be applied to the substrate by conventional means, for example, by dipping, spraying or brushing. The substrate may be a metal, but may be any other desired substrate and in any form.

A wide range of other additives may be incorporated into the compositions of the invention. Surface-active agents may be added to aid wetting. Pigments and/or non-refractory fillers may be added if desired. Plasticisers are useful when the settable refractory composition is used as a ramming or gunning mix, for example, bentonite and other clays or substitutes therefor, for example cellulose derivatives. Clays may also be used to increase the hot strength of the final product.

The invention is illustrated by the following Examples in which all parts are expressed as parts by weight.

EXAMPLES 1 AND 2

135 parts of anhydrous aluminium chloride were added slowly to 300 parts of water and to the resulting solution there were added 110 parts of 89% aqueous orthophosphoric acid. The resultant yellow solution was dehydrated in a co-current spray-drier having a spinning disc atomiser and a chamber at atmospheric pressure. Air inlet temperature was 140° and air outlet temperature was 70° C. A yellow water-soluble powder was produced which had the following analysis:

|  | Al | Cl | PO$_4$ | H$_2$O |
|---|---|---|---|---|
| % by weight | 11.4 | 17.4 | 39.3 | 30.0 |
| Proportion | 1.00 | 1.00 | 1.12 | 4.0 |

The powder will hereinafter be referred to as ACPH.

In two separate Examples 96 parts of graded Bauxite aggregate containing 1.2% by weight of iron were thoroughly mixed with 4 parts of high alumina clay, 5 parts of ACPH and 0.4 part of magnesium oxide setting agent (Magnorite 100F), and in the separate Examples there was added, respectively, 0.05 part (Example 1) and 0.1 part (Example 2) of inhibitor which is a mixture of compounds having the structure

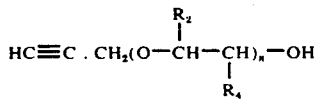

in which

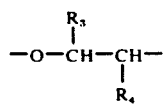

is a mixture of ethylene oxy and propylene oxy units and $n$ is on average 7.5. 6 parts of water were then added to each of the mixtures and the resultant doughs were cast into moulds having cavities of dimensions 4 inch × ½ inch × ½ inch, the doughs were allowed to set by standing for 15 minutes, and the resultant 4 inch × ½ inch × ½ inch test pieces were then removed from the moulds and heated at 110° C for 16 hours. The test pieces were then heated at a temperature of 1000° C for 2 hours. The test pieces, after removal from the moulds, showed a very small amount of bloating in the case of those produced from the mixture containing 0.05 part of inhibitor and the test pieces produced from the mixture containing 0.1 part of inhibitor showed no sign of bloating.

By way of comparison the above procedure was repeated except that the inhibitor was omitted. The resultant test pieces showed a considerable amount of bloating and in particular the top surface of the test pieces, which had not been constrained by the mould surfaces, was very porous and had been expanded above the level of the mould due to the formation of voids in the test pieces.

EXAMPLE 3

The procedure of Example 1 was repeated except that there was used 0.1 part of an inhibitor having the stucture

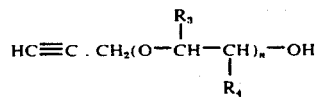

in which $n = 2$ and one of $R_3$ and $R_4$ is methyl and the other is hydrogen. The dimensions of the moulds which were used were 2½ inch × 2½ inch × 2½ inch, and the steps of heating at 110° and 1000° C were omitted. The test pieces removed from the moulds showed no sign of the formation of voids due to bloating.

By way of comparison the above procedure was repeated except that the inhibitor was omitted. In this case the test ieces removed from the moulds were porous due to bloating, and the top surfaces of the test pieces which had not been constrained by the mould surfaces were porous and had expanded above the level of the mold. Because of the bloating the test pieces had a volume 11% greater than the volume of the test pieces made from the composition containing inhibitor.

EXAMPLE 4

The procedure of Example 2 was repeated except that 0.05 part of inhibitor was used. In the resultant test pieces there was no sign of bloating.

EXAMPLE 5

The procedure of Example 3 was repeated except that there was used 0.1 part of an inhibitor having the structure

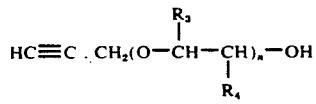

in which $n = 2$ and both of $R_3$ and $R_4$ are hydrogen. In the test pieces removed from the moulds there was no sign of bloating.

EXAMPLE 6

The procedure of Example 5 was repeated except that 0.05 part of inhibitor was used. In the resultant test pieces there was no sign of bloating.

We claim:

1. A mixture comprising at least one binder for a refractory aggregate which binder is a halogen-containing complex phosphate of aluminium containing one or more chemically-bound molecules of water and/or one or more chemically-bound molecules of an aliphatic alcohol containing from 1 to 4 carbon atoms, and at least one bloating inhibitor which is an acetylenic alcohol having the structure

                              1.

where $R_1$ and $R_2$, which may be the same or different, are selected from hydrogen atoms and alkyl groups having from 1 to 10 carbon atoms, Y is an oxyalkylene group, and $n$ is an integer in the range 2 to 30.

2. A mixture as claimed in claim 1 in which the groups $R_1$ and $R_2$ are both hydrogen atoms.

3. A mixture as claimed in claim 2 in which the oxyalkylene group has the structure

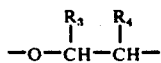

where $R_3$ and $R_4$, which may be the same or different, the selected from hydrogen atoms, alkyl groups having from 1 to 10 carbon atoms, substituted alkyl groups, and aromatic groups.

4. A mixture as claimed in claim 1 in which $n$ is on average a number in the range 2 to 12.

5. A mixture as claimed in claim 2 in which the group Y comprises oxyethylene or oxypropylene groups or a mixture thereof.

6. A mixture as claimed in claim 4 in which $n$ is on average approximately 7.

7. A mixture as claimed in claim 1 in which the binder comprises a chlorine-containing complex phosphate of aluminium.

8. A mixture as claimed in claim 1 in which the complex phosphate of aluminium contains from 1 to 5 molecules of chemically-bound water.

9. A mixture as claimed in claim 1 in which the number of gram atoms of aluminium to the number of gram atoms of phosphorus in the complex phosphate of aluminium is in the range 0.8:1 to 1.2:1.

10. A mixture as claimed in claim 8 in which the complex phosphate of aluminium has the empirical formula $AlPClCH_{11}O_9$.

11. A mixture as claimed in claim 1 which contains 0.2% to 5% of inhibitor by weight of the binder.

12. A mixture as claimed in claim 1 which contains a liquid diluent in which the binder and inhibitor are soluble.

13. An essentially dry refractory composition comprising a refractory aggregate and a mixture of a binder and an inhibitor as claimed in claim 1.

14. An essentially dry refractory composition as claimed in claim 13 in which the binder is present in the composition in a proportion of 0.5% to 40% by weight of the composition.

15. A settable refractory composition comprising a refractory aggregate, a mixture of a binder and an inhibitor as claimed in claim 1, and a liquid diluent which is a solvent for the binder and for the inhibitor.

16. A settable refractory composition as claimed in claim 15 in which the liquid diluent is present in a proportion of 0.5% to 25% by weight of the composition.

* * * * *